(12) United States Patent
Robl

(10) Patent No.: US 8,337,490 B2
(45) Date of Patent: Dec. 25, 2012

(54) APPARATUS FOR MOVABLE AND WEIGHT-COMPENSATING SUSPENSION OF A FOCUSING OBJECTIVE OF A LASER SYSTEM

(75) Inventor: Gerhard Robl, Stein (DE)

(73) Assignee: Wavelight AG, Erlangen (DE)

( * ) Notice: Subject to any disclaimer, the term of this patent is extended or adjusted under 35 U.S.C. 154(b) by 406 days.

(21) Appl. No.: 12/716,884

(22) Filed: Mar. 3, 2010

(65) Prior Publication Data

US 2011/0218523 A1    Sep. 8, 2011

(51) Int. Cl.
*A61B 18/18*    (2006.01)
(52) U.S. Cl. .............................. 606/4; 606/13
(58) Field of Classification Search ........... 606/4–13, 606/17, 107
See application file for complete search history.

(56) References Cited

U.S. PATENT DOCUMENTS

| | | | |
|---|---|---|---|
| 5,013,311 A * | 5/1991 | Nouri | 606/4 |
| 5,171,242 A * | 12/1992 | Dewey et al. | 606/4 |
| 5,226,903 A * | 7/1993 | Mizuno | 606/17 |
| 5,336,215 A | 8/1994 | Hsueh et al. | |
| 2010/0042081 A1* | 2/2010 | Rathjen | 606/5 |

FOREIGN PATENT DOCUMENTS

| | | |
|---|---|---|
| AU | 528966 | 5/1980 |
| EP | 1886639 | 2/2008 |

OTHER PUBLICATIONS

European Patent Office, International Search Report dated Sep. 30, 2010, Application No. PCT/EP2010/001319, 13 pages.

* cited by examiner

*Primary Examiner* — Mohammed Hasan
(74) *Attorney, Agent, or Firm* — Haynes and Boone, LLP

(57) ABSTRACT

An apparatus for movable weight-compensating suspension of a focusing objective of a laser system comprises a force generation device to generate a counterforce component $\overline{G}$ which counteracts the weight of the focusing objective, a transmission device which transmits the counterforce component $\overline{G}$ onto the focusing objective and permits upward/downward compensatory movement of the focusing objective, in such a way that in the case of an upward/downward compensatory movement of the focusing objective, an optical axis (O) of the focusing objective maintains at least its orientation in space, and preferably its position in space.

13 Claims, 1 Drawing Sheet

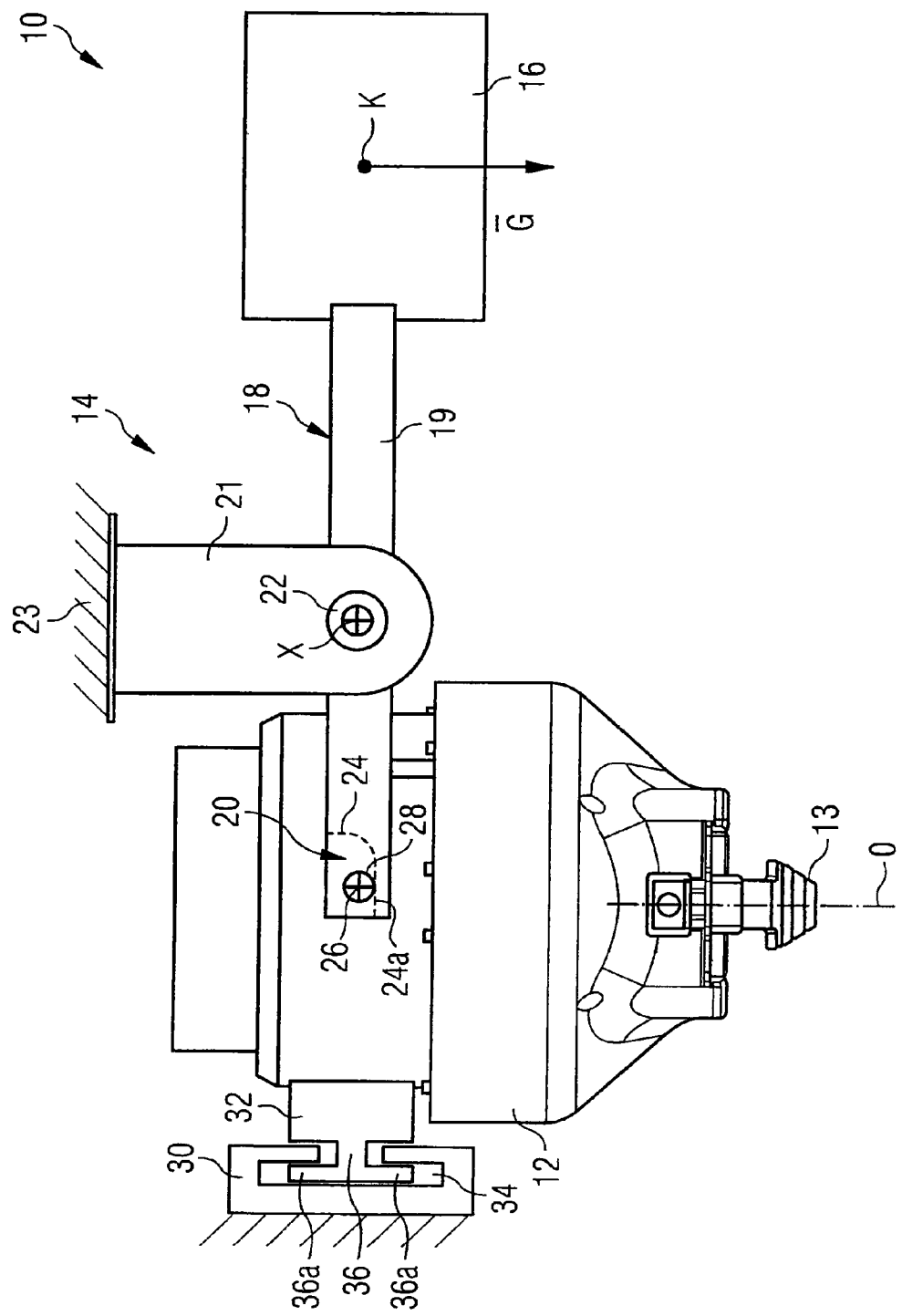

APPARATUS FOR MOVABLE AND WEIGHT-COMPENSATING SUSPENSION OF A FOCUSING OBJECTIVE OF A LASER SYSTEM

FIELD OF THE INVENTION

The invention concerns movable weight-compensating suspension of a focussing objective of a laser system. The laser system preferably provides pulsed laser radiation, which is focussed by means of the focussing objective onto a desired location where the radiation is to act.

BACKGROUND OF THE INVENTION

Movable weight-compensating suspension of the focussing objective is desired, not exclusively but above all, where treatment of living tissue is involved, and there is direct contact between the tissue and the laser system. Such direct contact is often produced, for example, in the case of operations on the human eye using laser surgery, when incisions in the cornea or other parts of the eye are to be made using ultra-short pulses of laser radiation. In this case, direct contact is intended to ensure precise positioning of the eye to be treated relative to the laser system in the direction of propagation of the radiation. Usually, a suitable interface unit (patient adapter) is connected in front of the focussing objective, and effects the physical coupling of the eye to the laser system. The interface unit usually has a holder, which is coupled to the focussing objective, for a contact element which is to be brought into contact with the eye and is made of a material which is transparent to the laser radiation. The contact element can, for example, be a plane underside for applanation of the cornea.

Focussing objectives in laser systems are often multi-lens systems, which can put considerable weight on the scales. Several kilograms are not unusual for such focussing objectives. Obviously, in an eye operation the full weight of the focussing objective must not rest on the eye being treated. Weight-compensating suspension for the focussing objective is therefore provided. The force which the focussing objective still exerts on the eye in the case of such a weight-compensating solution is reduced to a few newtons (e.g. 1 to 2 N), for example. This makes it possible to deflect the focus-sing objective upward, gently and not dangerously to the eye, if the patient suddenly happens to raise his or her head involuntarily, e.g. in a panic reaction.

An example of weight-compensating suspension of a focussing objective is given in U.S. Pat. No. 5,336,215. There the weight of the objective is compensated for by a spring system, by means of which the objective is movably suspended in a frame relative to the latter.

SUMMARY OF THE INVENTION

It is an object of the invention to give a reliably and precisely functioning solution for weight compensation of a focussing objective in a laser system.

According to the invention, for this purpose movable weight-compensating suspension of a focussing objective of a laser system is provided, comprising:
- a force generation device to generate a counterforce component which counteracts the weight of the focussing objective,
- a transmission device which transmits the counterforce component onto the focussing objective and permits upward/downward compensatory movement of the focussing objective, and
- a guidance device for movable guidance of the focussing objective, in such a way that in the case of an upward/downward compensatory movement of the focussing objective, an optical axis of the focussing objective maintains at least its orientation in space, and preferably its position in space.

Guidance of the focussing objective through the guidance device prevents undesired tilting of the optical axis of the objective in the case of an upward/downward compensatory movement of the objective. "Upward/downward compensatory movement" is understood here as a movement of the focussing objective upward or downward relative to the laser system. Thus despite a compensatory movement of the objective, the optical axis remains in a specified orientation to the object which is being treated, e.g. to the optical axis of a human eye which is being treated. It should be pointed out here that the invention can in principle be used with laser systems for any application purposes, and in particular for working on any materials (including dead matter), and is by no means restricted to ophthalmological application purposes.

The force generation device can include a counterweight, the mass of which is used to generate at least part, and in particular the whole, of the counterforce component. The counterweight can consist of a single counterweight member, or alternatively can consist of multiple (at least two) individual weight members, which for example can be used in changeable numbers or/and in changeable position relative to each other. The individual weight members can also be combined into a single total weight, and taken individually out of the total weight. By such variabilities of the counterweight, specially precise taring of the weight compensation is possible.

Moreover, within the invention, generating part of the counterforce component by means of at least one elastic element should not be excluded. Because of the disadvantage, which is often associated with elastic elements, that the effective force depends on the distance (the elasticity depends on the state of deformation of the elastic element), the force generation device preferably does not generate the counterforce component exclusively by means of elastic elements. However, combining one or more elastic elements with a counterweight is also conceivable, e.g. to implement a desired force-distance dependency intentionally. The transmission device is preferably in the form of a rocker, on one side of which the counterforce component acts, and on the other side of which the weight of the focussing objective acts. Functionally, the rocker can be compared with a weighing beam.

For example, the rocker is formed of at least one lever body, one lever arm of which is connected to the focussing objective, and the other lever arm of which is connected to the force generation device. It is understood that two or more such lever bodies can be provided adjacently, parallel and at a distance, to form the rocker. A force application point of the force generation device on the lever body can be adjustable along it, so as to adjust the torque acting on the lever body. In general, preferably at least one force application point of the force generation device on the rocker can be adjusted with respect to its distance from a swivelling axis of the rocker.

Use of a counterweight which is applied on one side of the rocker (i.e. on one lever arm) to generate at least part of the counterforce component has the advantage of the maximum possible constancy of the generated counterforce component over the whole operationally required movement travel of the focussing objective. By intentional displacement of the centre of gravity of the counterweight relative to the rocker, the force-distance characteristic curve of the suspension apparatus can be set definitively. This makes taring possible even with an indivisible counterweight. On the other hand, if the force generation device includes at least one elastic element, the force-distance characteristic curve of the suspension apparatus can be set in addition to the typically spring-like force-distance characteristic of the elastic element, because the force application point of the elastic element is movable along the lever or along the rocker.

The focussing objective is preferably supported on the rocker so that it can rotate relative to the rocker around an axis of rotation which runs parallel to a swivelling axis of the rocker at a distance. It is recommended, for spatial positional stability of the optical axis of the objective, that the support of the focussing objective on the rocker is at a variable distance to the swivelling axis of the rocker. If the rocker is tilted, the focussing objective can then carry out a simultaneous movement, meaning a change of distance from the rocker axis. In this way the objective can move up and down along a straight line instead of along a circular path, i.e. it maintains its transverse position (transverse means orthogonal to the objective axis) relative to the object being worked on.

The swivelling bearing of the rocker is preferably of low-friction form, and can for example be implemented by means of a plastic sliding bearing or a rolling bearing. Low friction is a desirable aim, to avoid, as far as possible, falsification of the effective force-distance characteristic of the suspension apparatus by overlaid friction forces.

In a preferred embodiment, the focussing objective is supported on a supporting surface arrangement of the rocker so that it can move freely. In particular, the sup-porting surface arrangement can be in such a form that the objective can be placed loosely on the rocker. The supporting surface arrangement can, for example, be formed of at least one longitudinal recess—into which the objective can be inserted with a suitable supporting pin or other supporting formation—of at least one lever body of the rocker. For example, the recess can be open upward, or/and it can—in relation to the longitudinal extent of the relevant lever arm, on which the objective grips—be open to the front or rear, so that the supporting formation of the objective can be inserted from the front or rear into the recess.

It is understood that the supporting surface arrangement can alternatively, for example, be in the form of an arrangement of one or more enclosed long holes, the objective engaging with each long hole by a suitable supporting projection. It is also understood that according to a modification, the supporting surface arrangement can be formed on the objective, and suitable supporting formations for support on the supporting surface arrangement can be formed on the rocker.

In any case, the support of the objective on the rocker is preferably such that not only rotation of the objective relative to the rocker in the course of a swivelling movement of the rocker is made possible, but also a radial change of the distance between the axis of rotation of the objective and the rocker axis (radially in relation to the rocker axis).

The guidance device is preferably in the form of a linear guide with a parallel guidance direction to the optical axis of the focussing objective. It preferably has guidance formations which prevent movements of the focussing objective transversely to the optical axis in the case of an upward/downward compensatory movement of the focussing objective. This is useful for stabilising the position of the objective in space.

For example, the guidance device can include a linear bearing and a slide which is guided in it. The slide can be fixed on the focussing objective. The linear bearing can also include at least one guidance groove. The slide can also include at least one guidance projection, which is set up to work with the guidance groove in such a way that movement of the slide in a horizontal direction is avoided. In this way, guidance of the focussing objective in a vertical direction is made possible, the optical axis of the focussing objective being able to maintain its alignment and position in the case of a compensatory movement of it relative to an initial position. For this purpose, the guidance groove can be formed with an undercut, into which the guidance projection engages.

According to another point of view, the invention provides a laser system, comprising:

a laser radiation source, preferably of pulsed laser radiation, a focussing objective for focussing the laser radiation the focussing objective having an optical axis, an interface unit, which is arranged on the radiation exit side of the focussing objective and is preferably separably coupled to it, with a contact element, which is transparent to the laser radiation, for placing on an object on which work is to be done using the laser radiation, a suspension apparatus, in particular of the type described above, for movable weight-compensating suspension of the focussing objective, this apparatus having a rocker, with two rocker arms, which is supported on a housing member so that it can be swivelled around a rocker axis of the laser system, the focussing objective being supported on one of the rocker arms so that it can rotate relative to the rocker around a parallel axis of rotation to the rocker axis, and on the other rocker arm a counterweight to generate a counterforce component which compensates for at least a predominant part of the weight of the focussing objective being attached, and the apparatus also having a guidance system for linearly movable guidance of the focus-sing objective along the optical axis thereof.

BRIEF DESCRIPTION OF THE DRAWINGS

FIG. 1 illustrates a weight compensating suspension apparatus according to one aspect of the invention.

The invention is further explained below, on the basis of the attached drawing. FIG. 1 shows, schematically and not at all to scale, an embodiment of a laser system for making incisions in the cornea or other tissue parts of a human eye.

DETAILED DESCRIPTION

Of the laser system, which as whole is marked with 10, only the "output stage" is shown in the drawing, i.e. essentially only a focussing objective 12 with a patient adapter 13 arranged on the radiation exit side of it. The focussing objective 12 is weight-compensated and movably suspended by a suspension apparatus 14. If "weight compensation" is mentioned here, it means compensation for at least a pre-dominant part of the weight of the objective 12. A particularly small residual part of the objective weight can remain without compensation, e.g. of the order of magnitude of a few newtons of weight. The focussing objective 12 focusses, in a way which is not shown in more detail, an afocal beam of rays of the laser radiation pro-vided by the laser system 10 onto a focus location within the eye tissue to be cut. The laser radiation which is used has, for example, pulse durations in the femtosecond range, and a wavelength in the low infrared range (e.g. between approx. 1000 and approx. 1100 nm), or in the UV range, preferably above about 300 nm.

The suspension apparatus 14, in the shown embodiment of FIG. 1, has a force generation arrangement with a counterweight 16, which generates a vertically directed weight component $\overline{G}$, with which it is intended that the weight of the focussing objective 12 should be at least partly compensated for. The suspension apparatus 14 also includes a transmission arrangement in the form of a rocker 18, which at its right-hand end in FIG. 1 is separably joined to the counterweight 16, whereas at its other, left-hand end in FIG. 1 it has a bearing seat 20 for separable coupling with the focussing objective 12. The counterweight 16 can be shifted along the appropriate lever arm of the rocker, so that the effective force application point K of the counterweight, and thus the effective counter-force moment, can be changed.

The rocker 18 is carried by a bearing 22 so that it can rotate around a swivelling axis X at a distance between the points of application of the objective 12 and of the counterweight 16. The bearing 22 supports the rocker 18, via one or more connecting cheeks 21, on a schematically indicated supporting part 23, which itself can be arranged stationarily or movably relative to other components of the laser system 10.

The rocker 18 can have, for example, an oblong, in particular essentially straight lever rod 19, which at one of its ends is coupled to the objective 12, and at its other end is coupled to the counterweight 16. Purposefully, two such lever rods 19 are provided, parallel to each other, on both sides of the objective 12 (i.e. behind and in front of the objective 12 in the viewing direction of FIG. 1). However, in the further description only one lever rod will be mentioned, but the following explanations apply analogously to both lever rods.

In the shown example the above-mentioned bearing seat 20 is formed by a laterally made recess 24 of the lever rod 19 (indicated by a dotted line), which is open on more than one side, that is upward and to the left in the FIGURE. The floor 24a of this recess 24 forms a supporting surface for a vertical journal 26 which stands laterally away from the objective 12 and projects into the recess. The focussing objective 12 rests loosely on the lever rod 19 via its vertical journal 26. If the rocker 18 is swivelled, not only is the objective 12 rotated around the journal axis relative to the rocker 18, but also the vertical journal 26 is displaced within the bearing seat 20. With this displacement, the radial distance of the vertical journal 26 from the swivel-ling axis X changes. This makes it possible, despite upward or downward movement of the objective 12, to keep the position and orientation of an optical objective axis O in space unchanged. So that the displacement of the vertical journal 26 in the bearing seat 20 takes place without friction as far as possible, for example the vertical journal 26 can carry a ring 28, which can roll on the floor 24a of the recess 24, on a sliding or rolling bearing.

The suspension apparatus 14 also includes a guidance system for vertical linear guidance of the focussing objective 12. Whereas the possibility of displacing the vertical journal 26 in the bearing seat 20 creates the precondition for a constant position in space of the objective axis O when the objective 12 moves, the guidance system ensures that the objective axis O is actually not tilted or displaced transversely (to the axis O).

The guidance system, in the shown embodiment, includes a linear bearing 30 which is fixed relative to the focussing objective 12, and a slide 32 which is guided on it and fixed on the focussing objective 12. The linear bearing 30 is provided with a guidance groove 34, which is in the form of an undercut and engages with a guidance projection 36 of the slide 32. The guidance projection 36 is T-shaped in cross-section in the embodiment shown in FIG. 1, the two T side arms 36a of the guidance projection 36 engaging with the undercut guidance groove 34 in such a way that a horizontal (transverse) movement of the focussing objective 12 away from the linear bearing 30 (to the right in FIG. 1) is prevented. Additionally, the engagement of the T side arms 36a with the undercut guidance groove 34 ensures that the focussing objective 12 does not tilt. It is always held by the guidance arrangement in a specified orientation.

The engagement of the guidance projection 36 with the guidance groove 34 provides sufficient vertical play to ensure the necessary movement travel of the focussing objective 12 in the vertical direction.

If the focussing objective 12, with its patient adapter 13, is placed on the eye (not shown) to be treated, the focussing objective 12 can be deflected vertically upward by a slight counter-pressure caused by the eye. In the case of this compensatory movement of the focussing objective 12, the vertical journal 26 shifts by rolling (or alternatively sliding) along the floor 24a of the recess 24, while the rocker 18 rotates clockwise around the rocker axis X, and simultaneously the objective 12 rotates relative to the rocker 18 around the axis of the vertical journal 26. In contrast, if, in an imaginary hypothetical case, the focussing objective 12 was joined rigidly to the rocker 18, an upward or downward movement of the focussing objective 12 would result in tilting the optical axis O. However, in the shown embodiment, such tilting is excluded, because of the movable support of the objective 12 on the rocker 18, and because of the linear guidance of the objective 12 by the linear bearing 30.

The invention claimed is:

1. Apparatus for movable weight-compensating suspension of a focusing objective of a laser system, comprising:
   a force generation device to generate a counterforce component which counteracts the weight of the focusing objective;
   a transmission device which transmits the counterforce component onto the focusing objective and permits upward/downward compensatory movement of the focusing objective; and
   a guidance device for movable guidance of the focusing objective, in such a way that in the case of an upward/downward compensatory movement of the focusing objective, an optical axis of the focusing objective maintains at least its orientation in space.

2. Apparatus according to claim 1, wherein the force generation device includes a counterweight, the mass of which is used to generate at least part of the counterforce component.

3. Apparatus according to claim 1, wherein the transmission device is in the form of a rocker, on one side of which the counterforce component acts, and on the other side of which at least part of the weight of the focusing objective acts.

4. Apparatus according to claim 3, wherein at least one force application point of the force generation device on the rocker can be adjusted with respect to its distance from a swivelling axis of the rocker.

5. Apparatus according to claim 3, wherein the focusing objective is supported on the rocker so that it can rotate relative to the rocker around an axis of rotation which runs parallel to a swivelling axis of the rocker at a distance.

6. Apparatus according to claim 5, wherein the support of the focusing objective on the rocker is at a variable distance to the swivelling axis of the rocker.

7. Apparatus according to claim 1, wherein the guidance device is in the form of a linear guide with a parallel guidance direction to the optical axis of the focusing objective.

8. Apparatus according to claim 7, wherein the guidance device has guidance formations which prevent movements of the focusing objective transversely to the optical axis in the case of an upward/downward compensatory movement of the focusing objective.

9. A laser system comprising:
   a laser radiation source;

a focusing objective for focusing the laser radiation, the focusing objective having an optical axis and a radiation exit side;

an interface unit, which is arranged on the radiation exit side of the focusing objective, with a contact element, which is transparent to the laser radiation, for placing on an object on which work is to be done using the laser radiation; and a weight-compensating suspension system coupled to the focusing objective, said system having at least two rocker arms supported on a housing member of the laser system so that the rocker arms can be swivelled around a rocker axis, the focusing objective being supported on one of the rocker arms so that it can rotate relative to the rocker arm around a parallel axis of rotation to the rocker axis, and on the other rocker arm a counterweight to generate a counterforce component which compensates for at least a predominant part of the weight of the focusing objective being attached, and the apparatus also having a guidance system for linearly movable guidance of the focusing objective along the optical axis thereof.

10. The laser system of claim 9, wherein the laser source produced pulsed laser radiation.

11. A method of performing laser eye surgery, comprising:

providing a surgical laser system having a focusing objective portion coupled to a laser radiation source, a counterweight and a rocker arm assembly joining the two components, the rocker arm pivotally coupled to a housing;

positioning a patient adjacent the focusing objective;

aligning an optical axis of the focusing objective with an optical axis of an eye; and advancing the focusing objective along the optical axis toward the eye by, at least in part, rotating the focusing objective with respect to the rocker arm.

12. The method of claim 11, further including moving the counterweight a distance proportional to the distance travelled by the focusing objective along the optical axis.

13. The method of claim 11, further including contacting the focusing objective of the eye with a predetermined force, and positioning the counterweight to move if a force greater than the predetermined force is applied on the focusing objective.

\* \* \* \* \*